United States Patent [19]

Bicker et al.

[11] Patent Number: 5,055,290

[45] Date of Patent: Oct. 8, 1991

[54] CIAMEXONE AS A SELECTIVE IMMUNOSUPPRESSANT

[75] Inventors: Uwe Bicker, Bensheim; Wulf Pahlke, Mannheim, both of Fed. Rep. of Germany

[73] Assignee: Boehringer Mannehim GmbH, Mannheim, Fed. Rep. of Germany

[21] Appl. No.: 198,790

[22] Filed: May 25, 1988

Related U.S. Application Data

[63] Continuation-in-part of Ser. No. 810,513, Dec. 18, 1985, abandoned.

[51] Int. Cl.$^5$ .............................................. A61K 39/00
[52] U.S. Cl. .................................... 424/85.8; 424/88; 514/340; 514/825; 514/866; 514/903
[58] Field of Search ............... 514/340, 885, 825, 903, 514/866; 424/85.8, 88

[56] References Cited

PUBLICATIONS

Fahey et al., Annal of Internal Medicine, 106, 1987, pp. 257–274.
Filipovich et al., Immunology Today, vol. 4(2), 1983.
Immunology, ed Roitt, 1985, pp. 23.2–23.3.
Bicker, Chapter 21 g, Immune, Modulation Agents and Their Mechanism, ed. Fenichel et al., 1984, pp. 447–473.
Bicker et al., "Journal of Immunopharmacoloty", 7(1): 127–139 (1985).
Katz, "The Immune System: An Overview", pp. 13–20.
Cooper et al., "B Lymphocytes", pp. 43–55.
Webb et al., "Immunosuppression, Immunopotentiation, & Anti-Inflammatory Drugs", pp. 277–292.
Roitt, "Immunology", 23.11 & 8.3.
Stites et al., "Basic & Clinical Immunology", pp. 430–459.
Rothfield, "The Journal of Clinical Investigation", vol. 46, No. 11 (1967).
"Bulletin on the Rheumatic Diseases", vol. 24, pp. 756–761.
Abruzzo et al., "IgG Anti-IgG Antibodies in Rheumatoid Arthritis and Certain Other Conditions", pp. 258–261.

*Primary Examiner*—Garnette D. Draper
*Attorney, Agent, or Firm*—Felfe & Lynch

[57] ABSTRACT

A method of selectively suppressing the excess immune reaction produced iatrogenically or autochthonously by administering 0.1 to 100 mg of ciamexone per kg of body weight.

11 Claims, No Drawings

CIAMEXONE AS A SELECTIVE IMMUNOSUPPRESSANT

This application is a continuation-in-part of application Ser. No. 810,513, filed Dec. 18, 1985, and now abandoned.

The present invention involves a method for suppression of excess immune reaction, produced iatrogenically or autochthonously in a subject, via administration of ciamexone, i.e., (2-cyano-1-[2-methoxy-6-methylpyridin-3-yl)-methyl]-aziridine. This compound is described in U.S. Pat. No. 4,410,532 (Bosies, et al.), which discloses N-substituted aziridine-2-carboxylic acid derivatives in general, and which is incorporated by reference herein. Also incorporated by reference is U.S. Pat. No. 4,397,848, also to Bosies, et al. which also teaches N-substituted aziridine-2-carboxylic acids.

The surprising feature of this invention is that ciamexone has been found to work as an immunosuppressant. Both the '532 and '848 patents describe the compounds referred to therein as immunostimulants.

It is important to understand the meaning of the terms "immunostimulant" and "immunosuppressant" as employed herein. "Immunostimulants" are substances which strengthen normal or suppressed immune systems in a specific manner such as by activating macrophages, T-lymphocytes, or B-lymphocytes. Immunostimulation is desirable whenever a stronger immunological response is necessary.

"Immunosuppression" on the other hand, involves suppression of immune reactions. Such suppression is dosage related, and involves all immunecompetent cells. An example of an immunosuppressant is cyclosporin (i.e., "Cyclosporin A), which suppresses adjuvant T-lymphocytes, as well as other T-lymphocytic immune reactions, and, when administered in large dosages, immune processes which are not T-cell related.

Yet a third group of drugs which act on the immune system are the immunomodulators. This last group strengthens some immune reactions, but suppresses others. Immunomodulation is extremely difficult to provie experimentally. See, e.g., Kirk Othmer: Encyclopedia of Chem. Tech. 13: 171 et seq. (1981; John Wiley and Son, N.Y.).

Immunosuppression, as defined herein, is useful, e.g., in preventing the body's normal rejection response to grafts of foreign tissue. Additionally, immunostimulation is desirable in connection with diseases which involve elevated levels of antibody production or monocyte-lymphocyte reactivity, occurring as a result of a hyperreactive immunoregulatory network. Such hyperreactivity is associated very closely with auto-immune diseases. See, in this regard, Mellbye, et al. Clin. Exp. Immunol 8: 889 (1971), (rheumatoid arthritis); Tourtellote, et al., Science 154: 1044 (1966) (multiple sclerosis); Abdou, et al., Clin, Immunol Immunopath 6: 192 (1976) (systemic lupus erythematosis); Witeboky, et al., J. Immunol 103: 708 (1969) (thyroiditis); Sharp, et al., Am. J. Med. 52: 148 (1972) (mixed connective tissue disease); Venables, et al., Ann. Rheum. Dis. 40: 217 (1981) (dermato/poly-myositis); Charles, et al., J. Immunol 130: 1189 (1983) (insulin dependent diabetes).

An immunosuppressant, if it is to be useful, must suppress only pathologically augmented immune processes. Suppression of normal immune processes, or immune processes that are functioning at levels below normal, such as in ARC/HIV infected persons, can be fatal.

Hence it is an object of this invention to provide a method for selectively immunosuppressing pathologically augmented immune processes without affecting other immune processes, by administering an immunosuppressive effective amount of ciamexone (2-cyano-1-[(2-methoxy-6-methylpyridin-3-yl)-methyl]-aziridine) to a subject, such as a human, in need of selective immunosuppression. The method is useful in treating those conditions associated with hyperreactive immunoactivity, including all of those conditions listed supra. How the objectives of the invention are achieved will become clear in the description which follows.

DETAILED DESCRIPTION OF PREFERRED EMBODIMENTS

It has now been found that ciamexone specifically suppresses excess autochthonic or iatrogenic immune reactions without interfering with normal immunoactivity, in a dosage related manner. It does so by inhibiting excess B-cell proliferation in the subject.

B-cells, it will be recalled, are antibody producers, and are involved in the branch of the immune system known as the humoral immune system, as compared to the cell mediated immune system, principally the domain of T-cells.

B-cell proliferation is caused by B-cell growth factor; hence, it may be said that ciamexone suppresses BCGF-induced B-cell proliferation.

B-cell proliferation requires stimulation of resting B-cells. This stimulus involves two signals. See, e.g., Falkoff, et al., J. Immunol 129: 97 (1982); Ford, et al., Nature 294: 261 (1981); Maizel, et al., Proc. Natl. Acad. Sci. USA 80: 5047 (1983); Kehrl, et al., Immunol. Rev. 78: 75 (1984). The first signal is an activation signal, mediated by an antigen, e.g. The activation signal results ultimately in expression of cell surface receptors for BCGF by the B-cells. BCGF is known as a soluble, T-cell derived lymphokine, having a molecular weight of from 17,000 to 18,000. See, e.g., Muraguchi, et al., J. Immunol 129: 2486 (1982); Butler, et al., J. Immunol. 133: 251 (1984); Maizel, et al., Proc. Natl. Acad. Sci. USA 79: 5998 (1982). Expression of BCGF receptors provides the B-cell with the capacity to respond to the proliferation signal delivered by the BCGF. Thus, normal B-cells are driven from resting state to proliferative state by this two signal process. See, e.g., Perri, et al., Eur. J. Immunol 16: 350 (1986).

An experimental model which shows the effect of a given substance in an iatrogenically or autochthonously induced overshooting immune reaction is the local graft vs. host (GvH) reaction in mice, or the local host versus graft (HvG) reaction. This model was used in the following experiments, which showed that ciamexone suppresses hyperreactive immune systems by suppressing B-cell proliferation.

EXAMPLE

Local GvH reactions were induced in (C57Bl/6×Balb/c)F1 hybrid mice by injecting $5 \times 10^6$ parental (Balb/c) spleen cells into the foot pad of one hind leg. As a control, the same number of F1 spleen cells were injected into the control foot pad on the contralateral side. To study local HvG reactions, the same protocol is followed for parental Balb/c mice, only now the test foot pad was injected with spleen cells of the hybrid F1 mice, and the control was spleen cells of parental generation mice (Balb/c). The same number was used.

The existence and extent of either GvH or HvG reaction was measured using the popliteal lymph node assay. On either the fifth day (for the GvH reaction), or the third day (for the HvG reaction) after the injection of the foreign cells, the subjects popliteal lymph nodes were removed and weighed. Weight increase of the node on the experimental side as compared to the weight of the node on the control side shows the extent of the reaction of the immune cells to the foreign tissue, it being understood that increases in lymph node size result from B-cell proliferation. In order to test the drug ciamexone, it was administered to the animals at daily doses of 0.1 to 100 mg/kg, and compared to cyclosporin, administered in the same dosage. The treatment period was either for two days (for HvG tests), or four days (for GvH tests), i.e. one day before animal sacrifice.

| Compound | Dose mg/kg | $\Delta$ Lymph node weight (mg $\times 10^{-1}$) | | | |
|---|---|---|---|---|---|
| | | GvH | | HvG | |
| | | $\bar{x}$ | $s_{\bar{x}}$ | $\bar{x}$ | $s_{\bar{x}}$ |
| Control | PBS | 45.2 | 8.3 | 35.5 | 10.3 |
| Ciamexone | 0.1 | 36.3 | 6.1 | 35.5 | 4.8 |
| | 1.0 | 25.7 | 10.5 | 21.5 | 4.8 |
| | 10.0 | 11.3* | 4.1 | 12.7* | 3.1 |
| | 100.0 | 3.5* | 1.9 | 7.5* | 3.7 |
| Control | Olive Oil | 36.3 | 8.5 | 43.3 | 9.4 |
| Ciciosporin | 0.1 | 35.7 | 10.8 | 36.2 | 6.0 |
| | 1.0 | 17.7* | 4.2 | 26.7* | 11.4 |
| | 10.0 | 8.5* | 3.8 | 10.7* | 5.7 |
| | 100.0 | 2.3* | 1.6 | 2.5* | 1.9 |

*$p \leq 0.05$ (student's t-test)

These results show that ciamexone suppressed the GvH and HvG reaction in the same way as did cyclosporin. This is evidenced by the reduced increase in lymph node size when ciamexone is administered, as compared to the control. Note that the effect is dosage dependent—i.e., as the dose increases, the suppression does also, as is evidenced by the decrease in lymph node weight.

This is direct evidence of the suppression of B-cell proliferation, because it is known that the GvH and HvG models used herein result in the infiltration of B-lymphocytes into the popliteal lymph node. It is this infiltration that causes the weight increase of the node. Other possible modes of suppression are not possible, because the total number of spleen cells in the subject animals did not increase.

For the preparation of pharmaceutical agents, ciamexone is mixed in a manner that in itself with suitable pharmaceutical vehicle substances, granulated if desired, and, for example, pressed to tablets or dragee cores. The mixture can also be packed into capsules. If suitable adjuvants are added, a solution or suspension can be prepared in water or oil (e.g., olive oil) and used to make injection solutions, soft gelatine capsules, syrup or drops.

Since the active substance is acid-labile, the preparations are either provided with a coating that is soluble only in the environment of the small intestine, or adjuvants (antacids, e.g., magnesium oxide) are incorporated into the formulas, which are capable of reducing the stomach acid to a pH above 6.

The solid vehicle substance can be, for example, starches or starch derivatives, sugar, sugar alcohols, celluloses and cellulose derivatives, tensides, talc, highly disperse silicic acids, fatty acids of high molecular weight or their salts, gelatins, agar-agar, calcium phosphate, animal and vegetable fats or waxes, and solid polymers of high molecular weight (such as polyethylene glycols or polyvinyl pyrrolidone) can be used. If liquid active substances are to be made into tablets or capsules, vehicles such as phosphates, carbonates and oxides can also be used in addition to highly disperse silicic acid. Preparations suitable for oral administration can contain flavoring and sweetening substances if desired.

EXAMPLE

An especially suitable medicament as proven to be a film-coated tablet of the following composition:

| | Weight each [mg] |
|---|---|
| ciamexone | 100.000 |
| lactose.H$_2$O | 63.000 |
| poly(0-carboxymethyl)starch, sodium salt | 7.000 |
| poly(1-vinyl-2-pyrrolidone) 25,000 | 4.000 |
| poly(0-carboxymethyl)starch, sodium salt | 3.000 |
| microcrystalline cellulose | 20.000 |
| silicon dioxide, highly disperse | 1.500 |
| magnesium stearate | 1.500 |
| Core weight | 200.000 |

The film-coated tablets are then prepared in the usual manner by film dredging the ciamexone cores.

Film-coated tablets containing, e.g., 10 mg, 50 mg, 200 mg or 500 mg of the active agent are prepared in like manner.

The dosage of the ciamexone active agent depends on the age and sex of the individual and on the kind of treatment that is to be given.

In general about 0.1 to 100 mg of ciamexone per kilogram of body weight is administered daily. Preferred, however, are amounts of 5 to 40 mg/kg of body weight and especially 5 to 20 mg/kg. These amounts of active agent can be administered 1 to 3 times daily.

It will be understood that the specification and examples are illustrative but not limitative of the present invention and that other embodiments within the spirit and scope of the invention will suggest themselves to those skilled in the art.

We claim:

1. Method for selective immunosuppression of a disease selected from the group consisting of graft versus host disease, host versus graft disease, rheumatoid arthritis, diabetes, and systemic lupus erythrematosis, comprising administering to a subject with one of said diseases an amount of ciamexone sufficient to suppress excess B-cell proliferation associated with said disease in said patient without affecting other immune processes.

2. Method of claim 1, wherein said excess immune process is iatrogenic.

3. Method of claim 1, wherein said excess process is autochthonic.

4. Method of claim 1, wherein said ciamexone is administered in an amount ranging from 0.1 to 100 mg/kg of said subject's body weight.

5. Method of claim 1, wherein said ciamexone is administered in an amount ranging from 5 to 50 mg per kilogram of said subject's body weight.

6. Method of claim 1, wherein said ciamexone is administered in an amount ranging from 5 to 20 mg per kilogram of body weight of said subject.

7. Method of claim 1, wherein said ciamexone is administered to said subject 1 to 3 times per day.

8. Method of claim 1, wherein said excess B-cell proliferation results from a graft versus host or host versus graph rejection.

9. Method of claim 1, wherein said excess B-cell proliferation results from rheumatoid arthritis.

10. Method of claim 1, wherein said excess B-cell production results from diabetes.

11. Method of claim 1, wherein said excess B-cell production results from systemic lupus erythematosis.

* * * * *